United States Patent [19]

Warriner

[11] Plant 4,043

[45] Apr. 26, 1977

[54] ROSE PLANT

[75] Inventor: William A. Warriner, Tustin, Calif.

[73] Assignee: Jackson & Perkins Co., Medford, Oreg.

[21] Appl. No.: 622,844

[22] Filed: Oct. 16, 1975

[51] Int. Cl.[2] ..... A01H 5/00

[52] U.S. Cl. ..... Plt./20

[58] Field of Search ..... Plt./20–21

*Primary Examiner*—Robert E. Bagwill

*Attorney, Agent, or Firm*—Klarquist, Sparkman, Campbell, Leigh, Hall & Whinston

EXEMPLARY CLAIM

1. A new and distinct cultivar of rose plant of the hybrid tea class, substantially as herein shown and described, characterized particularly as to novelty by the unique combination of its vigorous, upright habit of growth, Cardinal Red flower color, pronounced fragrance, and large downward pointed thorns.

1 Drawing Figure

The present invention relates to a new and distinct cultivar of rose plant of the hybrid tea class which was originated by me by crossing the cultivar Fragrant Cloud, U.S. Plant Pat. No. 2,574 with pollen of the cultivar, Proud Land, U.S. Plant Pat. No. 2,737.

The primary objective of this breeding was to produce a new rose cultivar of the hybrid tea class, combining the color of the male parent, Proud Land, with the fragrance of the female parent, Fragrant Cloud. This objective was substantially achieved along with other desirable improvements as evidenced by the following unique combination of characteristics which are outstanding in this new cultivar and which distinguish it from its parent as well as from all other cultivars of which I am aware:

1. An upright, vigorous plant, similar in habit to the cultivar, Proud Land, and somewhat similar also in habit, flower form, and color to the cultivar, Mister Lincoln, U.S. Plant Pat. No. 2,370.
2. A generally red flower color close to Wilson's Cardinal Red at all stages.
3. A pronounced fragrance.
4. Large thorns which look downward which differ from those of Mister Lincoln which point straight outward.

Asexual reproduction of this new cultivar by budding as performed at Wasco, Calif., shows that the foregoing characteristics and distinctions come true to form and are established and transmitted through succeeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose cultivar with color terminology in accordance with *Wilson's Horticultural Color Chart*, except where ordinary dictionary significance of color is indicated.

Parentage: Seedling.

*Seed Parent.*—Fragrant Cloud, U.S. Plant Pat. No. 2,574.

*Pollen Parent.*—Proud Land, U.S. Plant Pat. No. 2,737.

Classification:

*Botanical.*—Rosa hybrid.

*Commercial.*—Hybrid tea.

FLOWER

Observations made from specimens grown at Irvine, Calif., September 1975.

Blooming habit: Continuous.

Bud:

*Size.*—Approximately one inch when petals start to unfurl.

*Form.*—Pointed ovoid.

*Color.*—When sepals first divide — near Oxblood Red (00823). When half blown; upper side of petals near Cardinal Red (822). Lower side of petals slightly lighter than Cardinal Red (822/3).

*Sepals.*—Color: Outer surface near Spinach Green (0960/3) overlaid with Garnet Brown (00918/3). Inner surface near Spinach Green (0960/3) with abundant white tomentum. Three appendaged sepals, heavily appendaged. Two unappendaged, sepals, hairy edged.

*Receptacle.*—Color: Near Spinach Green (0960/3) overlaid in part with Garnet Brown (00918/3). Shape: Deep funnel, sides being cylindrical. Size: Large. Surface: Smooth.

*Peduncle.*—Length: Medium. Surface: Slightly prickly. Color: Light green, with considerable overlay of Garnet Brown (00918/3). Strength: Stiff, erect, heavy.

*Opening.*—Outer edges recurve slightly.

Bloom:

*Size.*—Large. Average open size 3.5".

*Borne.*—Singly and several together.

*Stems.*—Long, strong.

*Form.*—When first open, high centered. Permanence: outer petal edges slightly curled.

*Petalage.*—Number of petals under normal conditions — 25–30.

*Color.*—Center of flower: upper side of petals near Cardinal Red (822). Reverse side of petals slightly lighter than Cardinal Red (822/3). Base of petals: small area at point of attachment yellow. General tonality from a distance near Cardinal Red (822).

*Variegations.*—Occasional white streak in midrib of one or a few outer petals.

*Discoloration.*—General tonality at end of third day: no change.

*Fragrance.*—Strong.

Petals:
*Texture.*—Thick.
*Shape.*—Nearly round.
*Form.*—Tips slightly recurved.
*Arrangement.*—Imbricated. Petaloids in center.
*Persistence.*—Drop off cleanly.
*Lastingness.*—On the plant — long. As cut flower — long.

Reproductive Parts:
*Anthers.*—Medium. Color — yellow. Arrangement — regular around styles.
*Filaments.*—Color — yellow.
*Pollen.*—Lemon yellow.
*Styles.*—Color — nearly white. Styles are unusually tomentose.
*Stigmas.*—Color — yellow.

PLANT

Form: Bush.
Growth: Very vigorous, upright, branching.
Foliage: Number of leaflets on normal mid-stem leaves, 5 or 7.
*Size.*—Large.
*Quantity.*—Normal.
*Color.*—New foliage: near Garnet Brown (00918/3). Old foliage: darker than Spinach Green (0960).

Leaflets:
*Shape.*—Oval.
*Texture.*—Upper side — leathery.

*Edge.*—Serrated.
*Serration.*—Single, large.
*Petiole.*—Rachis — Color — near Garnet Brown (00918/3) to green. Underside — prickles.
*Stipules.*—Medium, bearded.
*Disease Resistance.*—Normally resistant to mildew under normal growing conditions at Irvine, Calif.

Wood:
*New Wood.*—Color — Garnet Brown (00918/3). Bark — smooth.
*Old Wood.*—Color — green to brown. Bark — smooth.

Prickles:
*Quantity.*—On main stalks from base — ordinary. On laterals from stalk — ordinary.
*Form.*—Very broad base, hooked downward.
*Color when young.*—Brown.
*Position.*—Irregular.

Small Prickles:
*Quantity.*—On main stalks — few to none. On laterals — few to none.

I claim:

1. A new and distinct cultivar of rose plant of the hybrid tea class, substantially as herein shown and described, characterized particularly as to novelty by the unique combination of its vigorous, upright habit of growth, Cardinal Red flower color, pronounced fragrance, and large downward pointed thorns.

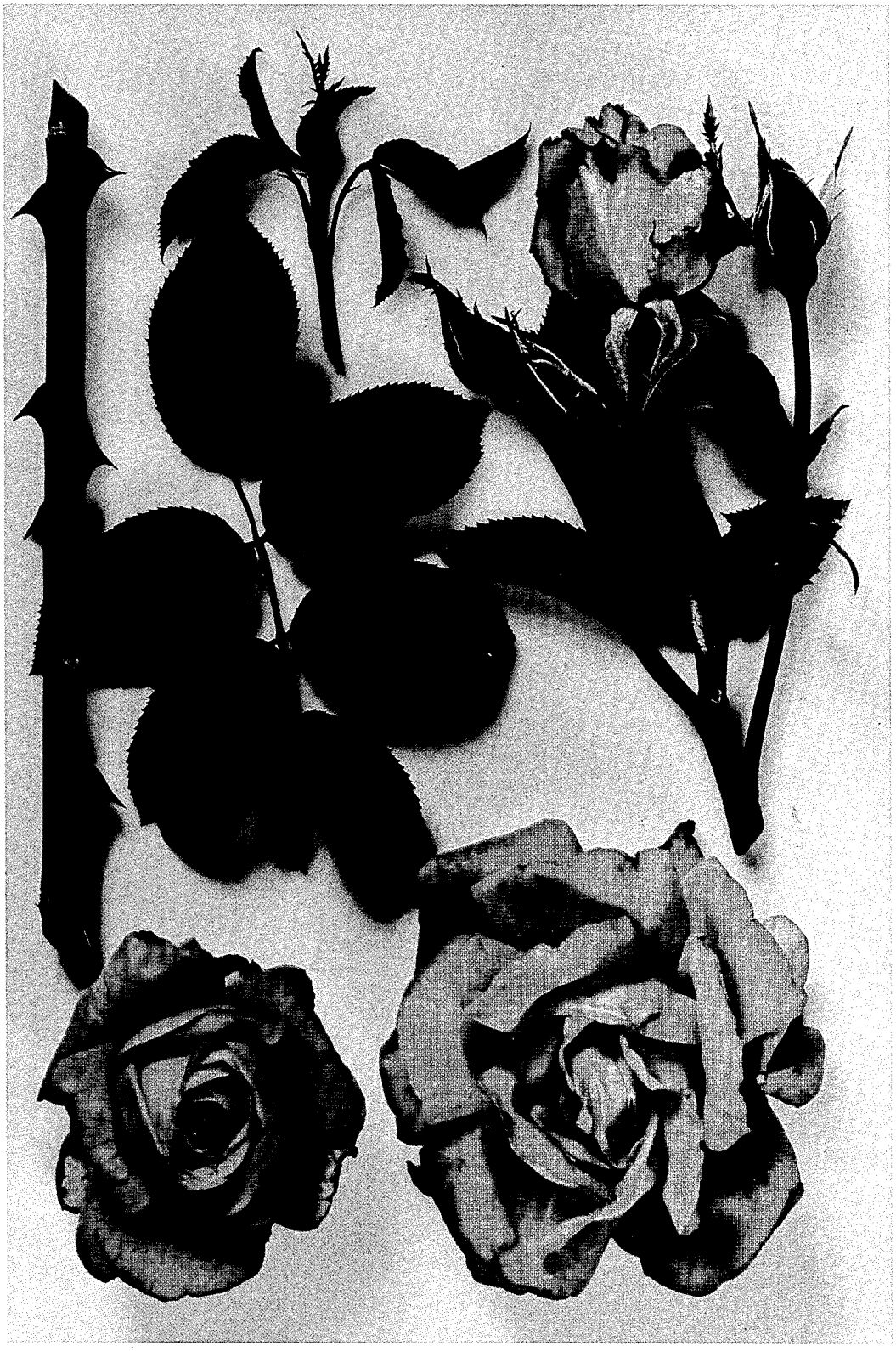

* * * * *